(12) United States Patent
Dennis et al.

(10) Patent No.: US 6,303,286 B1
(45) Date of Patent: Oct. 16, 2001

(54) SYSTEM AND METHOD FOR EMULATING AN IN VIVO ENVIRONMENT OF A TISSUE SPECIMEN

(75) Inventors: Robert G. Dennis, Ann Arbor; Paul Kosnik, Bay City, both of MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/611,241

(22) Filed: Jul. 6, 2000

Related U.S. Application Data

(62) Division of application No. 09/206,588, filed on Dec. 7, 1998, now Pat. No. 6,114,164.

(51) Int. Cl.$^7$ .................................................. C12Q 3/00
(52) U.S. Cl. ........................... 435/3; 435/173.1; 73/781; 73/788; 73/805
(58) Field of Search .............................. 435/1.1, 3, 173.1, 435/366, 375, 284.1, 286.1, 287.1, 289.1; 73/781, 788, 805; 364/506, 507, 508, 512, 514, 550, 551.01; 128/733, 740, 774

(56) References Cited

U.S. PATENT DOCUMENTS

| | | | |
|---|---|---|---|
| 4,605,623 | * | 8/1986 | Malette et al. . |
| 4,940,853 | * | 7/1990 | Vandenburg et al. . |
| 5,153,136 | * | 10/1992 | Vandenburg . |
| 5,443,950 | * | 8/1995 | Naughton et al. . |
| 5,452,236 | * | 9/1995 | Lintilhac et al. .................... 364/550 |
| 5,618,718 | * | 4/1997 | Auger et al. . |
| 5,700,688 | * | 12/1997 | Lee et al. .......................... 435/287.1 |
| 5,882,929 | * | 3/1999 | Fofonoff et al. ...................... 435/395 |

OTHER PUBLICATIONS

Herman A. Vandenburg et al., Skeletal Muscle Growth is Stimulated by Intermittent Stretch–Relaxtion In Tissue Culture, The American Physiological Society, 1989, pp. C674–682.*
Herman A. Vandenburg, In Vitro Cellular & Developmental Biology, vol. 24, No. 7, Jul., 1998, pp. 609–619.*
Herman A. Vandenburg et al. In Vitro Cellular & Developmental Biology, vol. 25, No. 7, 1989, pp. 607–616.*
Shansky et al. In Vitro Cellular & Developmental Biology, Oct. 1997. pp. 659–661.*
Herman A. Vandenburg et al., The FASEB Journal, vol. 5, Oct. 1991, pp. 2860–2867.*
Herman A. Vandenburg et al., Human Gene Therapy (Nov. 10, 1996), pp. 2195–2200.*

* cited by examiner

Primary Examiner—David A. Redding
(74) Attorney, Agent, or Firm—Brooks & Kushman P.C.

(57) ABSTRACT

A system and method are provided for adaptively controlling a muscle tissue specimen in order to emulate its in vivo environment. The system includes at least one stimulator for stimulating the muscle tissue specimen based on an initial control signal, wherein the stimulation preferably includes electrical and/or mechanical stimulation. A response signal is generated based on a response of the muscle tissue specimen to the step of stimulating. The response signal preferably represents force production of the tissue specimen. A controller is provided for modifying the initial control signal based on the response signal to obtain a final control signal, wherein the final control signal is used to elicit a desired response from the muscle tissue specimen. Advantageously, the system and method of the present invention can be used to adaptively control the stimulation of a muscle tissue specimen in a tissue culture environment.

12 Claims, 2 Drawing Sheets

SYSTEM AND METHOD FOR EMULATING AN IN VIVO ENVIRONMENT OF A TISSUE SPECIMEN

This is a divisional of application Ser. No. 09/206,588 filed on Dec. 7, 1998 now U.S. Pat. No. 6,114,164.

TECHNICAL FIELD

This invention relates to a system and method for providing adaptive control of the stimulation of a muscle tissue specimen in order to emulate its in vivo environment.

BACKGROUND ART

At present, three-dimensional tissues are capable of being produced in vitro using various types of cells. For example, U.S. Pat. No. 5,443,950 issued to Naughton et al. describes three-dimensional cultures for bone marrow, skin, liver, vascular, and pancreatic tissues which are grown within synthetic matrices. In these tissues as well as others, investigators have been successful in proliferating cells and tissues in vitro such that the resulting three-dimensional tissues, termed "organoids" or "constructs", display many of the characteristics of their in vivo counterparts. These constructs have a variety of foreseeable applications, ranging from transplantation in vivo to functional and pharmacological testing in vitro.

In the case of skeletal muscle constructs grown in vitro, the cells generally remain in a developmentally arrested state. To maximize the usefulness of skeletal muscle constructs for basic research, clinical diagnostic applications, and pharmaceutical screening, it would be desirable to promote and control the development of the constructs, in particular the induction of full differentiation of the muscle fibers, such that the constructs more closely mimic their in vivo counterparts.

To this end, the scientific literature indicates that interventions such as the application of controlled mechanical strain and transverse electrical fields are involved in the promotion of the correct orientation and differentiation of skeletal muscle cells in culture. Applying this knowledge, there are systems that allow the application of different mechanical strain patterns to cells in culture. See, for example, U.S. Pat. Nos. 4,940,853 and 5,153,136 issued to Vandenburgh.

However, these existing cell culture systems have several deficiencies. First, the systems focus on only one type of intervention, namely the application of mechanical strain. Furthermore, the systems are not capable of readily evaluating the contractile function of skeletal muscle constructs in vitro. Without the capability to detect tissue function or properties, present systems are forced to employ preprogrammed, open-loop control of strain parameters, and therefore are not able to knowledgeably adapt the strain parameters to changes in the development of individual tissue samples.

DISCLOSURE OF INVENTION

Therefore, it is an object of the present invention to provide a system and method for adaptively controlling the stimulation of a muscle tissue specimen in order to emulate its in vivo environment.

It is another object of the present invention to provide a system and method capable of integrating and applying multiple types of stimuli to a muscle tissue specimen to emulate its in vivo environment.

It is still another object of the present invention to provide a system and method for continuously monitoring the response of a muscle tissue specimen to stimulation.

Accordingly, a method is provided for emulating an in vivo environment of a muscle tissue specimen. The method includes stimulating the muscle tissue specimen based on an initial control signal. The method further includes generating a response signal based on a response of the muscle tissue specimen to the step of stimulating. In addition, the method includes modifying the initial control signal based on the response signal to obtain a final control signal, wherein the final control signal is used to elicit a desired response from the muscle tissue specimen.

To carry out the method of the present invention, a system is provided for emulating an in vivo environment of a muscle tissue specimen. The system includes at least one stimulator operable to apply stimulation to the muscle tissue specimen based on an initial control signal. The system additionally includes means for generating a response signal based on a response of the muscle tissue specimen to the stimulation. Further, the system includes a controller capable of modifying the initial control signal based on the response signal to obtain a final control signal, wherein the final control signal is used to elicit a desired response from the muscle tissue specimen.

The stimulation preferably includes electrical or mechanical stimulation. Most preferably, these different types of stimulation can be applied simultaneously. In a preferred embodiment, the generating means includes a force transducer, and electrical and mechanical stimulation are provided by an electrical stimulator and a servomotor, respectively. The response signal preferably represents force production of the muscle tissue specimen. Advantageously, the system and method of the present invention can be used to adaptively control the stimulation of a muscle tissue specimen in a tissue culture environment.

The above objects and other objects, features, and advantages of the present invention are more readily understood from a review of the attached drawings and the accompanying specification and claims.

BEST MODE FOR CARRYING OUT THE INVENTION

The present invention provides a system and method for emulating an in vivo environment of a muscle tissue specimen. In general terms, the method of the present invention includes stimulating the muscle tissue specimen based on an initial control signal, generating a response signal corresponding to a response of the muscle tissue specimen to the step of stimulating, and modifying the initial control signal based on the response signal to obtain a final control signal, wherein the final control signal is used to elicit a desired response from the muscle tissue specimen. This method represents closed-loop, adaptive control of the stimulation of the muscle tissue specimen, and can be implemented to be an automatic and continuous process.

To carry out the method of the present invention, a system is provided that utilizes an adaptive architecture including, in general terms, a tissue specimen, one or more sensors, one or more effectors, and a controller. In the emulator system of the present invention, the specific sensors and effectors employed will depend both upon the specific tissue type used, as well as the desired experimental conditions, interventions, and evaluation procedures. The tissue specimen could comprise a tissue construct developed in vitro from primary cell culture or, alternatively, native tissue excised from an animal or human being. As an example, the system and method of the present invention will be described in the context of promoting the growth and development of a skeletal muscle tissue specimen.

Figure 1:
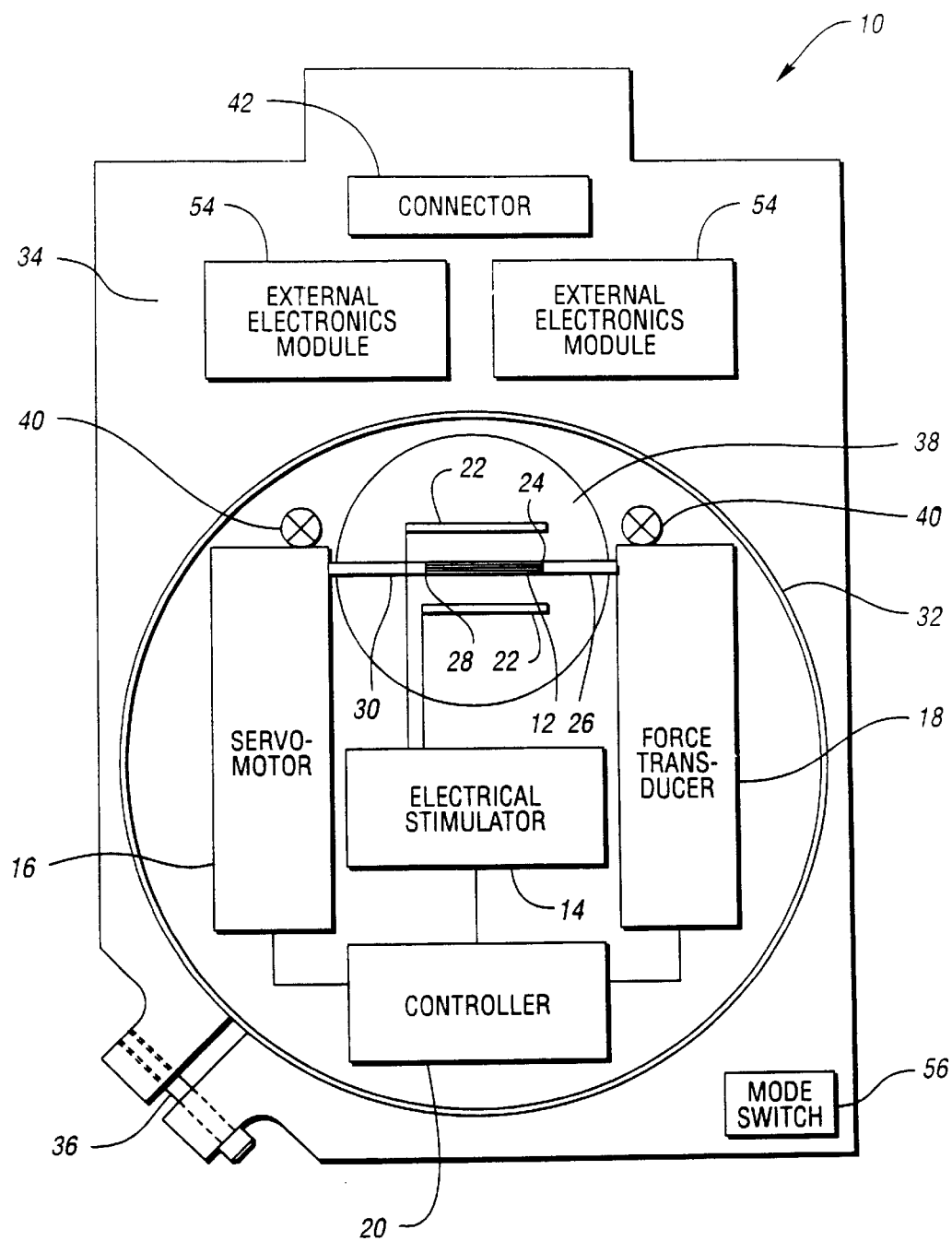
FIG. 1 is a top, schematic view of an emulator system constructed in accordance with the present invention.

Referring first to FIG. 1, shown is a schematic representation of a preferred embodiment of the emulator system of the present invention, which is designated generally by the reference numeral 10. A muscle tissue specimen 12 is acted upon and its responses are sensed. Emulator system 10 preferably can provide at least two effectors, or stimuli, to the muscle tissue specimen. Most preferably, the effectors include electrical stimulation and mechanical strain, and can be applied either individually or simultaneously. In a preferred embodiment shown in FIG. 1, electrical and mechanical stimulation are provided by an electrical stimulator 14 and a servomotor 16, respectively, based on an initial control signal.

Still referring to FIG. 1, a sensor is provided to generate a response signal corresponding to a response of muscle tissue specimen 12 to the electrical and/or mechanical stimulation. Preferably, the sensor comprises a force transducer 18 and force production is the response to which the response signal corresponds. Emulator system 10 further includes a controller 20, wherein controller 20 is preferably locally dedicated to muscle tissue specimen 12. Controller 20 analyzes the response signal from force transducer 18, allowing control decisions to be made based on the response signal. More specifically, controller 20 modifies the initial control signal of stimulator(s) 14 and/or 16 based on the response signal of force transducer 18 to obtain a final control signal for stimulator(s) 14 and/or 16. The final control signal can then be used to elicit a desired response, such as in the form of force production, from muscle tissue specimen 12. Controller 20 controls all electrical stimulation parameters, including pulse width, pulse frequency, amplitude, train duration, and % duty cycle. Controller 20 also controls the mechanical strain parameters, including strain rate, amplitude, and frequency.

As is well known in the art, electrical stimulation is typically used to activate skeletal muscle tissue. In the presence of electrical stimulation, the force produced by skeletal muscle tissue can be measured while the muscle is held at fixed length by servomotor 16, is allowed to shorten during the stimulation, or is forced to lengthen during the stimulation. During shortening, the power produced by the muscle tissue can be determined. In the absence of electrical stimulation, passive stiffness of the skeletal muscle can be measured.

In a preferred embodiment, electrical stimulator 14 should provide a purely bipolar stimulation pulse in order to eliminate electrolytic degradation of the culture medium and subsequent poisoning of the tissue. In the case of muscle tissue, the stimulation pulses from electrical stimulator 14 are applied via electrodes 22 placed parallel to muscle tissue specimen 12 on either side thereof to create a transverse electric field. Generally, however, electrode placement is dependent upon the desired stimulation protocol, tissue type, and tissue geometry. Electrodes 22 should be non-toxic to prevent contaminating the cell culture environment. Therefore, platinum wire or plate is preferred for the construction of electrodes 22.

Force transducer 18 is attached to a first end 24 of muscle tissue specimen 12 via a noncompliant arm 26. For use with a skeletal muscle tissue specimen 12 as in the present example, force transducer 18 preferably resolves forces of at least $1\,\mu N$ and measures forces up to about $3000\,\mu N$. Further, force transducer 18 preferably has a bandwidth of DC to 100 Hz, a full range deflection not exceeding 1 % of the length of muscle tissue specimen 12, and a power dissipation of less than 50 mW. In addition, force transducer 18 is preferably constructed to be insensitive to high humidity, permitting use in a tissue culture environment. Of course, the preferred properties of force transducer 18 will depend on the specific tissue type used with emulator system 10.

As shown in FIG. 1, an opposite end 28 of tissue specimen 12 is preferably attached to servomotor 16 via a servomotor arm 30. In the type of servomotor 16 depicted herein, servomotor arm 30 is actuated by a rack and pinion mechanism (not shown) and moves in a piston-like fashion in order to apply mechanical strain to muscle tissue specimen 12. The selection of an appropriate servomotor and gear mechanism depends upon the desired mechanical intervention. However, the motor selected should not have mechanical brushes, so that the production of ozone and other toxic byproducts of electrical arcs is avoided. Therefore, stepping motors or brushless DC motors would be appropriate choices for use in emulator system 10. The choice between these two types of motors will depend upon the system requirements, stepping motors generally being preferred in systems that require discrete and/or slow strains, and DC brushless motors being preferred when wide mechanical bandwidth is required, such as in high strain rate applications.

Other types of servomotors, such as d'Arsonval-type movements, as in a panel meter, may be employed within emulator system 10 when it is desired to control torque rather than displacement. In another embodiment, current from servomotor 16 could be used to determine the force production of muscle tissue specimen 12, thereby eliminating the need for force transducer 18.

As a low cost substitute for servomotor 16, a simple compliant anchor (not shown) may be used. The anchor could take the form of a cantilever, a coiled spring, or the like to subject tissue specimen 12 to a known load vs. displacement relationship. This arrangement may be particularly useful for all types of muscle tissue, since muscle tissue develops and maintains function much better when the tissue is able to produce mechanical work as well as significant mechanical displacements when activated. A compliant anchor could also be used when the dimensional changes are small, but constant loads are required, such as in the case of epithelial or bone tissue. When a compliant anchor is used, the response signal from force transducer 18 can be used to control electrical stimulation.

Controller 20 preferably includes electrical stimulation control electronics, servomotor control electronics, and force transducer signal conditioning electronics, all of which are integrated to provide adaptive control of stimulation parameters. The use of a local embedded controller 20 for each individual muscle tissue specimen 12 allows emulator system 10 to automatically modify and adapt the stimulation parameters to suit the needs of each individual tissue specimen 12 based upon its response to applied stimuli. Therefore, emulator system 10 is capable of continuously changing as the tissue develops, keeping with the normal circumstances in vivo in which the developing organism is constantly adapting to changes in the properties of the tissue of which it is comprised.

Still referring to FIG. 1, emulator system 10 preferably includes a main chamber 32 to house system components, such as in the form of a culture dish. In a preferred embodiment, a mounting plate 34 is provided to removably mount main chamber 32 therein. Mounting plate 34 is provided with a ring clamp 36 which may be adjusted for easy mounting and removal of main chamber 32. Within main chamber 32, a separate tissue chamber 38, such as a culture dish, is provided to hold muscle tissue specimen 12. Preferably, height adjustments 40 are provided to allow the height of servomotor 16 and force transducer 18 to be optimized for attachment to muscle tissue specimen 12. Optionally, a fluid perfusion system (not shown) may be provided in fluid communication with tissue chamber 38 to automate media changes or for the timed introduction of soluble chemical agents into tissue chamber 38.

Figure 2:
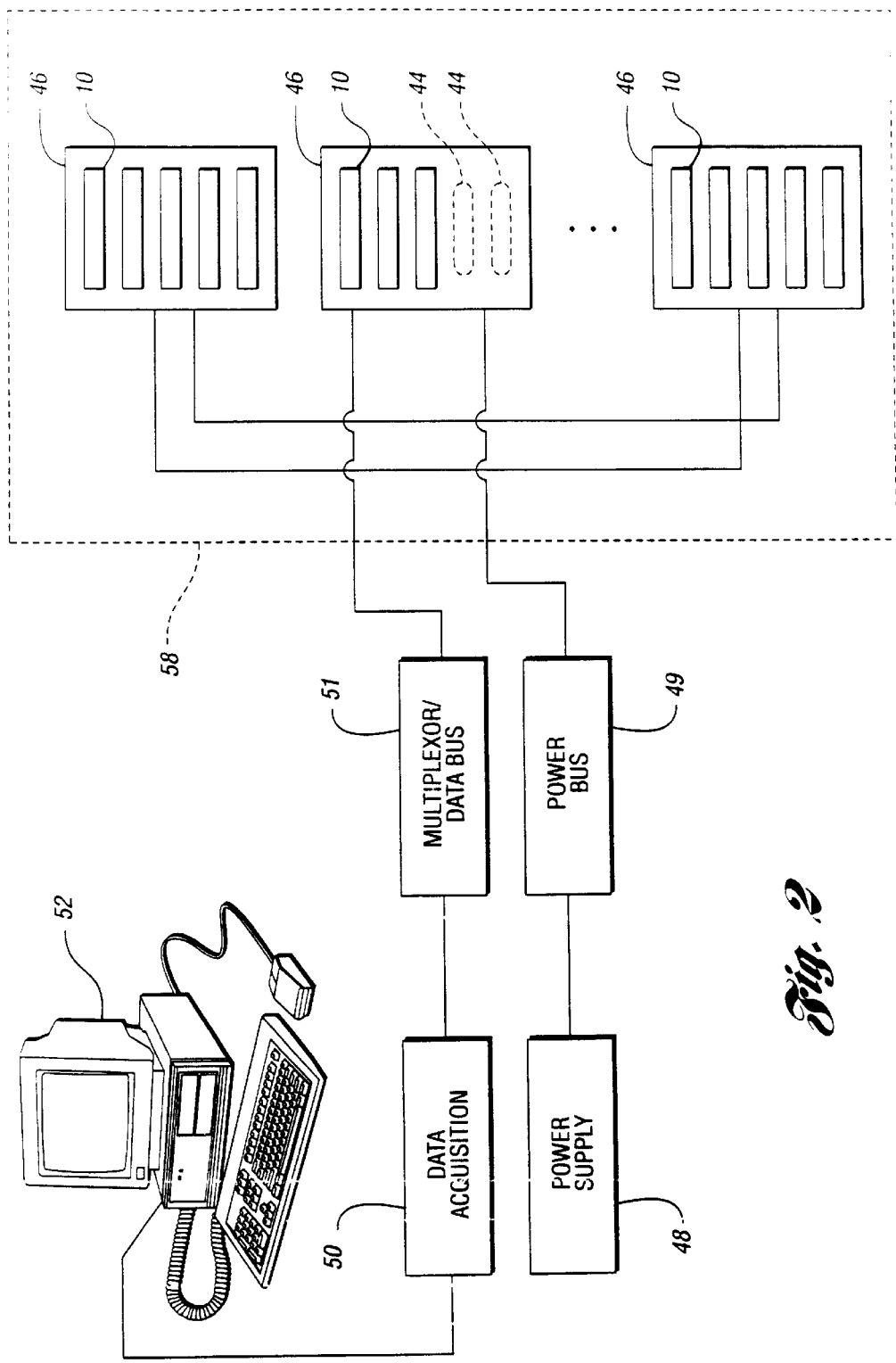
FIG. 2 illustrates a preferred configuration of the emulator system of FIG. 1 as it is interfaced with auxiliary instrumentation.

Mounting plate 34 further includes a connector 42, such as a standard D-sub connector, which may be fit into a mating opening 44 on a tower 46, as shown in FIG. 2. Tower 46 preferably provides each emulator system 10 with connections to an external power supply 48 through a power bus 49, a data acquisition system 50 through a multiplexor/bidirectional data bus 51, and an external processor 52, such as a personal computer. Locations for on-board electronics modules 54, such as a battery, an A/D converter, a signal processor, or a signal multiplexor are provided on mounting plate 34, such that local communication with controller 20 can be established. A mode switch 56 is provided on mounting plate 34 so that control of stimulation can be switched between the local control of controller 20 and external control provided through external processor 52.

For powering system components, emulator system 10 preferably uses a power supply 48 of +/−15V, +5V, which incorporates a regulated variable voltage supply of approximately 1.25 to 45 V DC. Current consumption is a function of the number of emulator systems 10 in use at one time. Emulator system 10 of the present invention further includes software, including servomotor control software, software governing experimental protocols, interface software, and temporary data acquisition and storage.

With reference to FIG. 2, one or more emulator systems 10 may easily be in operation simultaneously within a compact space. Multiple towers 46 may be used to accommodate several emulator systems 10 each, possibly within an incubator 58. Of course, emulator system 10 is scalable, and is therefore easily able to accommodate different tissue types and geometries.

Emulator system 10 of the present invention may be used for acute and chronic interventions for any type of in vitro or in situ experiment. Preferably, emulator system 10 is constructed so as to allow maintenance of muscle tissue specimens in culture under sterile conditions and to facilitate the use of normal cell culture equipment for care and feeding of the muscle tissue specimen when in culture.

Using emulator system 10 described above, two fundamental control loops can be implemented. Specifically, a response, preferably force production, of muscle tissue specimen 12 to applied stimuli is used by controller 20 to control both electrical and mechanical stimulation protocols through modification of control signals to electrical stimulator 14 and servomotor 16, respectively. Control algorithms can be generated to emulate the activation patterns and loading conditions that are experienced by muscle tissue during the normal development and locomotion of an organism. Because of the number of parameters that can be controlled, and the number of conditions under which contractile function can be measured, the actual number of variations for closure of the control loops and the number of degrees of freedom in the control algorithms is very large. However, several examples detailing system integration are given below, wherein the tissue specimen will be again taken to comprise skeletal muscle tissue.

As a first example, baseline functional parameters of muscle tissue specimen 12 can be determined using emulator system 10 of the present invention. For example, at regular intervals electrical stimulator 14 can apply a battery of pulses of variable amplitude to determine the rheobase, or voltage threshold of excitability, of muscle tissue specimen 12. Electrical stimulator 14 can then use the rheobase value in a series of pulses of variable pulse width to determine the chronaxie, or pulse-width excitability threshold, of muscle tissue specimen 12. Using this information, controller 20 can apply an adaptive algorithm by modifying the control signal to electrical stimulator 14 in order to maximally stimulate muscle tissue specimen 12 with minimal pulse amplitude and minimum pulse width. The stimulation parameters will be a function of the developmental stage of muscle tissue specimen 12, and may reflect such variables as the expression of neuromuscular junction proteins.

As a second example, the peak isometric contractile force of muscle tissue specimen 12 can be determined using emulator system 10. To obtain this measurement, electrical stimulator 14 applies a full tetanic stimulation to muscle tissue specimen 12 with servomotor arm 30 in a fixed position. Based on the peak isometric force, controller 20 could apply an adaptive algorithm to use servomotor 16 as a virtual spring, which becomes more stiff as muscle tissue specimen 12 develops greater contractile force generating capacity. For example, the position of servomotor arm 30 will be a direct function of the applied force, as dictated by Hooke's law ($F=-kx$). The spring constant ($k$) is programmed in software, and is determined by the adaptive algorithm and the measured value for peak isometric force. Alternatively, the algorithm could incorporate digitally-simulated non-linear springs and viscous loads. In addition, the length-tension relationship of muscle tissue specimen 12 can be established by moving servomotor arm 30 to stretch or shorten muscle tissue specimen 12, and at each point measuring the peak isometric force. Controller 20 can then modify the control signal to servomotor 16 to allow muscle tissue specimen 12 to shorten over a pre-determined range at any given level of stimulation.

For these and other examples, the system and method of the present invention provide integrated, adaptive control of the mechanical and electrical environment of a muscle tissue specimen to promote tissue growth and differentiation.

The adaptive algorithms for electrical stimulation and mechanical loading may be combined with open-loop algorithms. For example, controller 20 can employ an algorithm which applies a slow mechanical strain to the muscle tissue specimen 12, initiating at a certain time and having a slow positive strain rate that is fixed, and therefore not dependent on contractile function. This type of mechanical stimulation serves to emulate the effects of long bone growth and normal muscle loading on the limb muscles of a developing organism. As another example, electrical stimulator 14 can apply a low amplitude, continuous electric field to developing muscle tissue in order to pre-align myocytes.

Although the emulator system and method of the present invention have been described in the context of use with skeletal muscle tissue, the system is readily modified for emulating the development environment of different types of tissue or for tissues of different geometries. For example, the emulator system could be modified to accommodate such tissues as smooth or cardiac muscle, bone, tendon, ligament, cartilage, epithelial, or vascular endothelial tissue.

In addition to use with single type tissue specimens, emulator system 10 may be used to create a dynamic environment for tissue co-culture. Examples of co-culture tissue specimens include myoblast/fibroblast, epithelium/fibroblast, and muscle/nerve co-cultures. Emulator system 10 may be used to promote directed growth of tissues in co-culture, to facilitate the proliferation of first one, and then another of the tissues, or to control or detect the various stages of the development of the co-culture.

For example, there is evidence that muscle and nerve cells in culture will align perpendicularly with respect to one another in the presence of an applied electrical field. A muscle/nerve co-culture could be formulated in which the muscle/nerve interaction, in the form of a developed synaptic junction, is detected by an abrupt change in the excitability of the muscle tissue. Such a response is observed in vivo when muscle tissue has been reinnervated after a long period of denervation. This type of event would be detected easily in an automatic fashion by emulator system 10 of the present invention. In addition to notifying an operator that synaptic development had occurred, emulator system 10 could automatically modify the stimulation protocol to more closely meet the needs of an innervated muscle, such as reduced current and pulse width of stimulation.

As another example, a sample of epithelial tissue co-cultured with fibroblasts could be placed under controlled mechanical strain. The tissue could also be subjected to transverse electrical fields, which have been shown to accelerate wound closure under some circumstances. The tissue could be regularly subjected to controlled mechanical perturbations to measure its tensile properties. The application of slow negative strain may be used to simulate wound closure and possibly stimulate an apoptotic response in the fibroblasts. The fibroblast would be expected to necrose as a result, as typically occurs in wound contracture. When a change in the tensile properties of the tissue specimen indicated that the mechanical properties of the tissue had changed, such as due to the necrosis of fibroblasts, emulator system 10 could modify the mechanical environment of the sample to promote growth and differentiation of the remaining epithelial cells.

Although the emulator system and method of the present invention have been described largely in the context of emulating the conditions that occur during tissue growth and development, the system is easily configured to emulate unusual circumstances, such as periodic unloading or regular and extreme exercise. In addition, the emulator can be used to engineer a tissue to have the contractile properties desired for implantation or other use within the limits of the plasticity of that particular tissue.

Emulator system 10 of the present invention could also be used in clinical screening for congenital disease or for investigation into the effects of chemical stimuli. For instance, emulator system 10 could be utilized to determine the effect of a specific pharmacologic agent on development and/or function of skeletal muscle, to determine tissue-specific toxicity and dose-response curves, or to determine the tissue-targeted efficacy for drugs in the absence of systemic interactions.

It is understood, of course, that while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed.

What is claimed is:

1. A method of emulating an in vivo environment of a muscle tissue specimen, the method comprising:

electrically stimulating the muscle tissue specimen based on an initial control signal;

generating a response signal corresponding to a response of the muscle tissue specimen to the step of stimulating; and modifying the initial control signal based on the response signal to obtain a final control signal, wherein the final control signal is used to elicit a desired response from the muscle tissue specimen.

2. The method of claim 1, further including stimulating the muscle tissue specimen mechanically.

3. The method of claim 1, wherein the muscle tissue specimen includes skeletal muscle tissue.

4. The method of claim 1, wherein the response of the muscle tissue specimen comprises force production.

5. The method of claim 1, wherein the step of stimulating includes stimulating the muscle tissue specimen in culture.

6. The method of claim 1, further including stimulating the muscle tissue specimen chemically.

7. A method of emulating an in vivo environment of a tissue specimen, the method comprising:

electrically stimulating the tissue specimen based on an initial control signal;

generating a response signal corresponding to a response of the tissue specimen to the step of stimulating; and modifying the initial control signal based on the response signal to obtain a final control signal, wherein the final control signal is used to elicit a desired response from the tissue specimen.

8. The method of claim 7, further including stimulating the tissue specimen mechanically.

9. The method of claim 7, further including stimulating the tissue specimen chemically.

10. The method of claim 7, wherein the tissue specimen includes muscle tissue.

11. The method of claim 7, wherein the tissue specimen includes nerve tissue.

12. The method of claim 7, wherein the step of stimulating includes stimulating the tissue specimen in culture.

* * * * *